United States Patent [19]

Ponticello et al.

[11] Patent Number: 5,284,948

[45] Date of Patent: Feb. 8, 1994

[54] DRUG HAPTEN ANALOGUES FOR IMMUNOASSAYS

[75] Inventors: Ignazio S. Ponticello, Pittsford; Marsha D. B. Oenick; Susan J. Danielson, both of Rochester; David A. Hilborn, Henrietta, all of N.Y.

[73] Assignee: Eastman Kodak Company, Rochester, N.Y.

[21] Appl. No.: 851,435

[22] Filed: Mar. 16, 1992

Related U.S. Application Data

[63] Continuation-in-part of Ser. No. 712,329, Jun. 7, 1991, abandoned.

[51] Int. Cl.$^5$ .................. C07D 403/00; C07D 239/02; C07D 233/72
[52] U.S. Cl. .................................... 544/295; 544/300; 544/370; 548/316.7; 548/317.1; 548/318.1; 548/318.5; 548/319.1; 548/319.5; 548/320.1; 435/21; 435/25; 435/28; 436/501; 436/523
[58] Field of Search ............. 544/390, 300, 295, 370; 548/318.1, 319.1, 316.7, 317.1, 318.5, 319.5, 320.1; 540/575

[56] References Cited

U.S. PATENT DOCUMENTS

| | | | |
|---|---|---|---|
| 4,065,354 | 12/1977 | Ullman et al. | 548/308 |
| 4,092,479 | 5/1978 | Parsons, Jr. et al. | 548/312 |
| 4,182,856 | 1/1980 | Buckler | 548/314 |
| 4,413,002 | 11/1983 | Wootton | 548/309 |
| 4,670,381 | 6/1987 | Frickey et al. | 435/7 |
| 4,752,568 | 6/1988 | Danielson et al. | 435/7 |

OTHER PUBLICATIONS

Anderson et al, CA109-162790d (1988).
Barquet et al, CA104-65419d (1985).
Frina et al, CA99-2721d (1982).

*Primary Examiner*—Cecilia Tsang
*Attorney, Agent, or Firm*—John R. Everett

[57] ABSTRACT

The invention is directed to new drug hapten analogues comprising:
(A) an active ester group;
(B) a drug hapten nucleus selected from a hydantoin nucleus or a barbiturate nucleus and
(C) a linking chain linking the 3-position of the drug hapten nucleus to the active ester group.

3 Claims, No Drawings

DRUG HAPTEN ANALOGUES FOR IMMUNOASSAYS

This is a continuation-in-part of U.S. patent application No. 712,329 filed Jun. 7, 1991, now abandoned.

FIELD OF THE INVENTION

This invention relates to clinical chemistry, particularly immunoassays.

BACKGROUND OF THE INVENTION

Immunoassays, which take advantage of natural immunological reactions, have found wide-spread use as analytical techniques in clinical chemistry. Because of the specificity of the reactions, they are particularly advantageous in quantifying biological analytes that are present in very low concentration in biological fluids. Such analytes (called ligands herein) include, for example, antibodies, therapeutic drugs, narcotics, enzymes, hormones, proteins, etc.

In competitive binding immunoassays, a labeled drug hapten analogue is placed in competition with unlabeled drug haptens for reaction with a fixed amount of the appropriate antibody. Unknown concentrations of the drug hapten can be determined from the measured signal of either the bound or unbound (i.e. free) labeled drug hapten analogue.

Conventional labels include radioactive tags, enzymes, chromophores, fluorophores, stable free radicals, and enzyme cofactors, inhibitors and allosteric effectors.

Specific requirements for labeled drug hapten analogues (hereafter sometimes LDH) include: 1) at least 65% of the LDH can be bound by excess immobilized antibody; 2) affinity of the LDH for immobilized antibody is such that competition of a fixed amount of LDH with the drug occurs in a therapeutically relevant concentration range; and 3) stability of the LDH against hydrolysis of its enzyme label under storage conditions. Requirements imposed on the drug hapten analogues include: 1) accessibility of the analogue to the immobilized antibody following conjugation with the enzyme label; 2) specific recognition of the labeled analogue by the antibody to the drug; and 3) sufficient reactivity of the drug analogue with the enzyme label, either directly or following activation of the enzyme or analogue, under conditions that do not adversely affect enzyme activity.

Glucose oxidase (GOD) and alkaline phosphatase (ALP) enzyme labels coupled to barbiturate or hydantoin analogues disclosed in U.S. Pat. No. 4,752,568, especially phenobarbital and phenytoin analogues, gave adequate enzyme labeled analogues for conducting effective competitive immunoassays in the desired format.

The problem is that hydantoin and barbiturate analogues were unsatisfactory for conducting competitive immunoassays when the enzyme horseradish peroxidase (HRP) was used as the label. The coupling reactions between such derivatives and HRP were both slow and incomplete. Moreover, previous phenytoin-HRP and phenobarbital-HRP labels were bound very weakly so that much higher concentrations of label or antibody binding sites would be required to give a readable signal.

It would be highly desirable to provide new drug hapten analogues for barbiturates and hydantoins (a) that do react with HRP, and other enzymes such as GOD and ALP, faster and more completely, than prior art analogues, (b) to form covalent bonds with HRP, and (c) produce labeled drug hapten analogues that are more readily recognized and tightly bound by antibodies to such analogues.

SUMMARY OF THE INVENTION

The present invention provides new drug hapten analogues comprising:
(a) an active ester group, such as a succinimidoxycarbonyl;
(b) a nucleus selected from hydantoin or barbiturate derivatives;
(c) a linking chain linking the active ester group to the selected nucleus;
wherein the linking chain has about 5 to about 40 atoms consisting of (1) $C_1$ to $C_{10}$ alkylene groups, (2) phenylene groups, and (3) 5 to 7 membered heterocyclic rings (e.g., a 1,4-piperazinylene, 2,5-dimethyl-1,4-piperazinylene; 1,3-imidazolidinylene; and 1,3-hexahydrodiazepinylene group) joined into the linking group through ring nitrogen atoms, said groups and rings being bonded to each other through chemical groups selected from (a) esters, including thioesters, $$(-\overset{O}{\underset{\|}{C}}Z-), \text{ where } Z \text{ is } O \text{ or } S; \text{ (b) amides, } (-\overset{O}{\underset{\|}{C}}NH-),$$

(c) hetero atoms selected from $-O-$, $-S-$, and $-NR-$; wherein R represents $C_1$ to $C_6$ alkyl (e.g. methyl, ethyl, propyl, butyl etc.); and (d) carbonyl, with the proviso that the linking group is other than a derivative of a saturated or unsaturated monocarboxylic acid having from to 2 to 12 carbon atoms.

More specifically, the preferred new hydantoin and barbiturate active esters of this invention are those conforming to the structure:

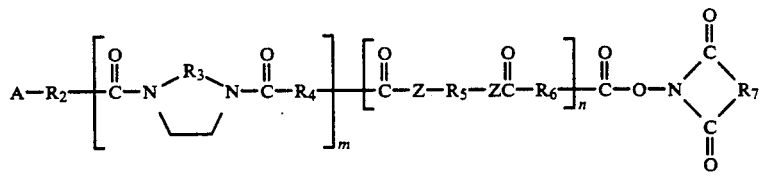

wherein
A represents a hydantoin nucleus of the

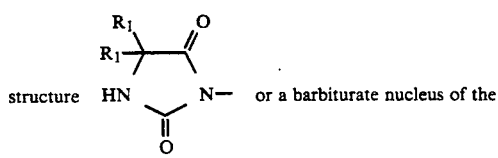

structure or a barbiturate nucleus of the structure 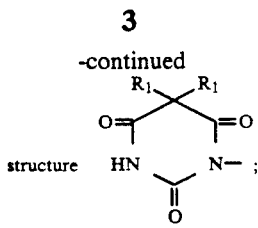

$R^1$ each independently represents hydrogen, alkyl of 1 to 10 carbon atoms, unsubstituted or substituted phenyl;

$R^2$, $R^4$, $R^5$, and $R^6$, each independently represents $C_1$ to $C_{10}$ alkylene or such alkylene groups interrupted with at least one or more ester groups, amide groups, —O—, —S—, and —NR—;

$R^3$ represents $C_1$ to $C_3$ alkylene;

$R^7$ is an ethylene or o-phenylene group;

Z represents —O—, —S—, and —NR—, wherein R represents hydrogen or $C_1$ to $C_6$ alkyl, e.g., methyl propyl and hexyl;

m is 0, 1, or 2;

n is 0, 1, or 2;

m+n is >0 and the total number of atoms comprised in m, n and $R^2$ is 5 to 40;

and further provided that (i) at least one of the $R^1$ groups is substituted or unsubstituted phenyl; (ii) one of $R^4$, $R^5$, and $R^6$ can be phenylene; (iii) the bracketed components of structure I can appear therein in any order and (iv) the linking group is other than a derivative of a saturated or unsaturated monocarboxylic acid having from to 2 to 12 carbon atoms.

Several advantages are realized by use of the above drug hapten analogues. First, it was found that the active esters of these analogues having short linking chains between the nucleus and the active ester group were sufficiently reactive with HRP to prepare an acceptable enzyme label for use with only some immobilized antibodies. Derivatives with longer linker groups ($R^2$ plus the bracketed groups) of 8 to 20 atoms between the active ester group and the nucleus gave labels that could be bound by all immobilized antibodies tested. Linking chains in which each Z is —NR— which with the adjacent carbonyl forms an amide group, are particularly useful in analogues of this invention because such chains are more resistant to hydrolysis than chains wherein Z is —O— or —S— so that with the adjacent carbonyl it forms an ester group.

DETAILS OF THE INVENTION

Methods of making the drug hapten analogues of this invention are presented below.

Hydantoin Drug Analogues

The hydantoin drug analogues can be made according to the following preparations in which phenytoin analogues, a species of hydantoin compounds, are made.

Example 1 —Preparation of HD 1, 5,5-Diphenyl-3-{4-[2-(3-succinimidoxycarbonylpropionyloxy)ethylaminocarbonyl]butyl}-hydantoin Step 1: preparation of 5,5-Diphenyl-3-[4-(2-hydroxyethylaminocarbonyl)-butyl]hydantoin Part A: First the Acid Chloride is prepared.

A mixture of 3-(4-carboxybutyl)-5,5-diphenyl-2,4-imidazolidinedione (3.52 g, 0.01 mole) thionyl chloride (20 mL), N,N-dimethylformamide (2 drops) and chloroform (50 mL) was stirred at room temperature for 3 hours. The solvent was removed on a rotary evaporator in vacuo, and this product was used directly in the next Part B.

Part B: The Acid Chloride is reacted with Ethanolamine.

The acid chloride in chloroform (50 mL) was added dropwise over 15 minutes to a mixture of ethanolamine (1.2 g, 0.02 mole) and triethylamine (2.4 g, 0.024 mole) in chloroform (100 mL). The mixture was then heated to 60° C. for 2 hours and stirred to room temperature for 1 hour. The solution was then washed with 5% hydrochloric acid (2×100 mL), washed with saturated sodium bicarbonate solution (100 mL), dried over anhydrous magnesium sulfate, filtered, and the solvent removed on a rotary evaporator. The filtrate was then chromatographed using an aluminum oxide column to give material (3.0 g) showing one spot on TLC. This material was used directly in the next preparation.

Step 2: preparation of 3-{4-[2-(3-Carboxypropionyloxy)ethylaminocarbonyl]-butyl}-5,5-diphenylhydantoin The hydroxy compound of Step 1 (3.0 g, 0.0075 mole), succinic anhydride (1.0 g, 0.01 mole), and dimethylaminopyridine (0.9 g, 0.0075 mole) in chloroform (100 mL) were heated at 50°-60° C. for 4 hours and allowed to cool to room temperature over the weekend.

Dichloromethane (300 mL) was added, and the mixture was washed with 5% hydrochloric acid solution (3×100 mL), washed with saturated sodium chloride solution (100 mL), dried over anhydrous magnesium sulfate, filtered, and the solvent removed to give a material that gave one spot on TLC.

Step 3: preparation of HD 1: 5,5-Diphenyl-3-{4-[2-(3-succinimidoxycarbonylpropionyloxy)ethylaminocarbonyl]butyl}hydantoin.

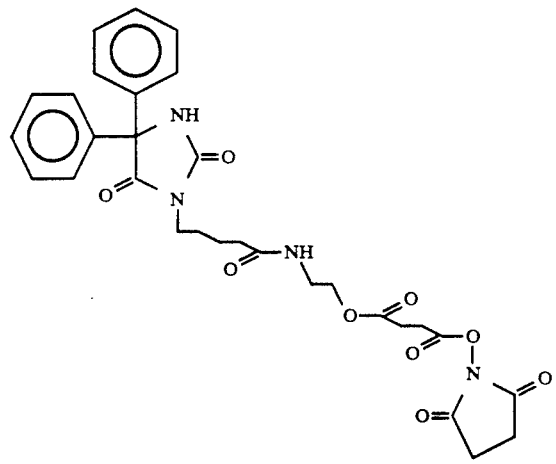

A mixture of acid from Step 2 (3.0 g, 0.006 mole), N,N'-dicyclohexylcarbodiimide (1.5 g, 0.007 mole), and N-hydroxysuccinimide (0.7 g, 0.006 mole) in chloroform (80 mL) was stirred at room temperature for 20 hours. The mixture was filtered, and the filtrate was concentrated on a rotary evaporator in vacuo. The residue was then chromatographed using silica to give 1.3 g (40% yield). Anal. calc. for $C_{30}H_{32}N_4O_9$: C, 60.8; H, 5.44; N, 9.45. Found: C 59.6; H, 5.51, N, 8.91

Example 2 —Preparation of HD 2:
5,5-Diphenyl-3-{4-[4-(3-succinimidoxycarbonylpropionyl)-1-piperazinylcarbonyl]butyl}-2,4-imidazolidinedione

Step 1: preparation of 5,5-Diphenyl-3-(1-piperazinylcarbonylbutyl)hydantoin Part A: First, 3-[4-(4-Benzyloxycarbonyl-piperazinylcarbonyl)butyl]-5,5-diphenyl-2,4-imidazolidinedione was prepared The acid chloride prepared as described in the preparation of HD 1, supra, Part A (0.01 mole) was added dropwise over 15 minutes to a mixture of benzyl 1-piperazinecarboxylate (2.4 g, 0.011 mole) and triethylamine (2.0 g, 0.02 mole) in chloroform (50 mL). This mixture was stirred at room temperature overnight, and dichloromethane (300 mL) was added The mixture was washed with 5% hydrochloric acid (2×100 mL), washed with dilute sodium carbonate solution (100 mL), washed with saturated sodium chloride solution (100 mL), dried over anhydrous magnesium sulfate solution, filtered, and the solvent removed on a rotary evaporator in vacuo. The filtrate was then chromatographed to give an oil, 4.3 g (78% yield) which was used directly in the next step.

Part B: The protected amine of Part A (4.8 g, 0.008 mole) and 30–35% hydrogen bromide acetic acid solution (25 mL) was allowed to stir at room temperature for 1.5 hours. This mixture was then poured into diethyl ether (1 L), and the oil which separated was triturated with fresh portions of ether (3×1 L). The oil was dissolved in 10% aqueous sodium hydroxide solution (pH=14) and the aqueous solution extracted with dichloromethane (4×100 mL). The combined organic solution was washed with saturated sodium chloride solution (150 mL), dried over anhydrous magnesium sulfate, filtered, and the solvent removed in a rotary evaporator in vacuo. The filtrate solidifies to give a white solid (2.6 g, 77% yield). This material was used directly in the next step.

Step 2: preparation of 3-{4-[4-(3-Carboxypropionyl)-1-piperazinylcarbonyl]butyl}-5,5-diphenyl-2,4-imidazolidinedione.

A mixture of the amine from Preparation 7 (2.1 g, 0.005 mole) and succinic anhydride (0.54 g, 0.0054 mole) in chloroform (15 mL) was heated for 30 minutes at 50°–60° C. and allowed to stand at ambient temperature for 20 hours. Dichloromethane (150 mL) was added, and the mixture was washed with 5% hydrochloric acid (2×100 mL), saturated sodium chloride solution (100 mL), dried over anhydrous magnesium sulfate, filtered, and the solvent removed on a rotary evaporator in vacuo to give a white solid, 2.5 g (95%) which was used directly in the next step.

Step 3: preparation of HD 2: 5,5-Diphenyl-3-{4-[4-(3-succinimidoxycarbonylpropionyl)-1-piperazinylcarbonyl]butyl}-2,4-imidazolidinedione.

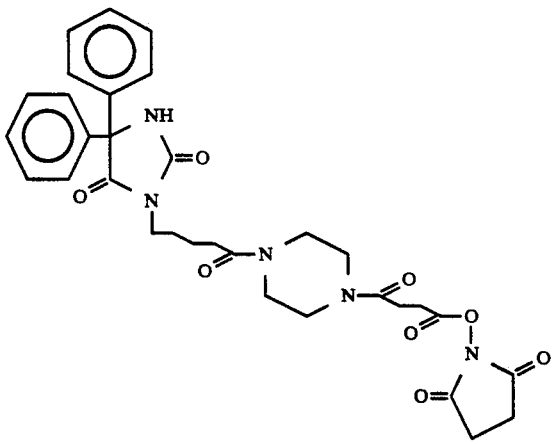

A mixture of the acid from step 2 (1.56 g, 0.003 mole), N,N'-dicyclohexylcarbodiimide (0.64 g, 0.003 mole), and N-hydroxysuccinimide (0.36 g, 0.003 mole) in chloroform (40 mL) was stirred at room temperature over the weekend. The mixture was filtered and the solvent removed from the filtrate on a rotary evaporator in vacuo to give 1.9 g (100% yield). The solid was chromatographed, and the product fraction was dissolved in dichloromethane (200 mL), washed with dilute sodium carbonate solution (2×100 mL), dried over anhydrous magnesium sulfate, filtered, and the solvent removed on a rotary evaporator to give a white solid which gives one spot on TLC. Anal. calc. for $C_{32}H_{35}N_5O_8$: C, 62,23; H, 5.71; N, 11.34. Found: C, 59.07; H, 5.40; N, 10.45.

Example 3 —Preparation of HD 3, 5,5-Diphenyl-3-{4-[6-(3-succinimidoxycarbonylpropionamido)hexylaminocarbonyl]butyl}-2,4-imidazolidinedione

Step 1: preparation of 3-[4-(6-Aminohexylaminocarbonyl)butyl]-5,5-diphenyl-2,4-imidazolidinedione Part A: preparation of 3-[4-(6-Benzyloxycarbonylaminohexylaminocarbonyl)-butyl]-5,5-diphenyl-2,4-imidazolidinedione The acid chloride prepared as an intermediate in the preparation of HD 1 was treated with N-benzyloxycarbonyl-1,6-hexanediamine by the procedures described in step 1 in the preparation of HD 2, to give 7.5 g, 85% yield, of the protected amine.

Part B: The protected amine of Part A was treated with hydrobromic acid-acetic acid by the procedures of Step 1, Part B in the preparation of HD 2, to give the free amine which was used in step 3 without purification.

Step 3: preparation of 3-{4-[6-(3-Carboxypropionamido)hexylaminocarbonyl]butyl}-5,5-diphenyl- 2,4-imidazolidinedione This compound was prepared using the same procedures as step 2 of the HD 2 preparation. Anal. Calc. for $C_{30}H_{38}N_4O_6$: C, 65.44; H. 6.96; N, 10.17. Found: C, 63.26, H, 7.01; N, 9.39.

Step 4: preparation of HD 3:
5,5-Diphenyl-3-{4-[6-(3-succinimidoxycarbonylpropionamido)hexylaminocarbonyl]butyl}-2,4-imidazolidinedione

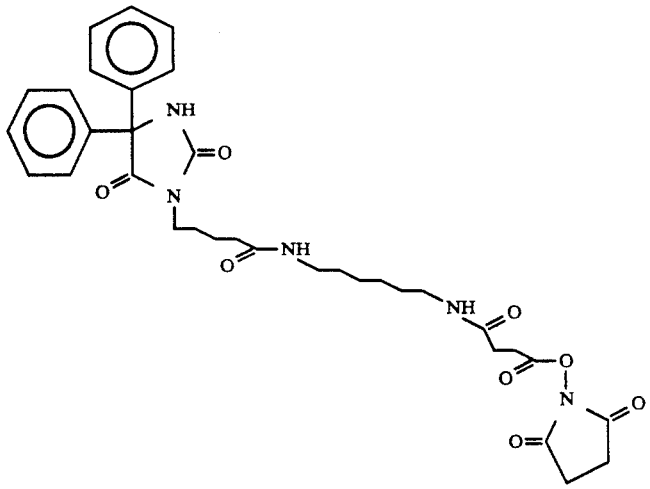

This material was prepared using the procedures of step 3 in the preparation of HD 2 to give 2.6 g (80% yield), mpt 133°–134° C. Anal. Calc. for $C_{34}H_{41}N_5O_8$: C, 63.05; H, 6.38; N. 10.81. Found: C, 62.91; H, 6.41; N, 10.69.

Barbiturate Drug Analogues

The following preparatory examples 4 to 8 illustrate the preparation of the barbiturate drug hapten analogues for phenobarbital. The analogues are generally prepared by (1) condensing a barbiturate derivative such, as phenobarbital, with an omega-haloalkanecarboxylate ester, (2) saponifying the ester to the corresponding acid, (3) conversion of acid the to the corresponding acid chloride, (4) condensation of the acid chloride with N-hydroxysuccinimide, or to further lengthen the linking chain, with a diamine, diol, or aminoalcohol having one of the amine or hydroxy groups blocked and (5) deblocking, condensation with a dicarboxylic acid such as succinic acid, and then condensation with the N-hydroxysuccinimide to produce the analogue.

If desired, the condensation with a half-blocked diamine, diol, or aminoalcohol, and then another diacid can be repeated once or twice more to further lengthen the linking chain. However, the same can be accomplished with fewer steps by using longer chained diacids, diols, diamines, amino alcohols, or haloalkanecarboxylate esters.

Example 4 —Preparation of PB 1:
5-Ethyl-5-phenyl-1-{4-[4-(3-Succinimidoxycarbonylpropionyl)-1-piperazinylcarbonyl]butyl}-2,4,6(1H,3H,5H)pyrimidinetrione

Step 1: Preparation of 5-Ethyl-6-hydroxy-3-(4-methoxycarbonylbutyl)-5-phenyl-2,4(3H,5H)-pyrimidinedione A mixture of phenobarbital (46.5 g, 0.2 mole) and tetrabutylammonium hydroxide (500 mL, 0.2 mole of 0.4M in water) in dichloromethane (500mL) was prepared and to it was added methyl 5-bromovalerate (39.0 g, 0.2 mole). The reaction mixture was stirred vigorously overnight (20 hrs). To this mixture was added saturated sodium chloride solution (100 mL), the organic layer was separated, and the aqueous solution was washed with dichloromethane (2×100 mL). The combined organic solution was washed with saturated sodium chloride solution (100 mL), dried over anhydrous $MgSO_4$, filtered, and the solvent removed.

Step 2: Preparation of 3-(4-Carboxybutyl)-5-ethyl-6-hydroxy-5-phenyl-2,4(3H,5H)-pyrimidinedione The 5-ethyl-6-hydroxy-3-(4-methoxycarbonylbutyl)-5-phenyl2,4(3H,5H)-pyrimidinedione ester (54.0 g, 0.156 mole) of step 1 in dioxane (500 mL), concentrated hydrochloric acid (55 mL), and water (55 mL) was heated at reflux for 4 hrs and at room temperature overnight. The dioxane was removed under reduced pressure, and saturated sodium chloride solution (250 mL) and dichloromethane (400 mL) were added to the residue. The organic layer was separated, and the aqueous solution was extracted with dichloromethane (3×150 mL). The combined organic solutions were washed with saturated sodium chloride solution (200 mL), dried over anhydrous $MgSO_4$, filtered, and the solvent removed. To the residue was added diethyl ether, and the mixture was placed in a freezer at −16° C. over the weekend, and then filtered.

Step 3: Preparation of 1-(4-chlorocarbonylbutyl)-5-ethyl-5-phenyl-2,4,6(1H,3H,5H)pyrimidinetrione A mixture of the acid (6.6 g, 0.2 mole) from preparation 2, thionyl chloride (50 mL), N,N-dimethylformamide (2 drops), and chloroform (80 mL) was stirred at room temperature for 1.5 hrs. The solvent was removed on a rotary evaporator in vacuo, and this product was used directly in the next step 4.

Step 4: Preparation of 1-[4-(4-Benzyloxycarbonyl-1-piperazinylcarbonyl)butyl]-5-ethyl-5-phenyl-2,4,6(1H,3H,5H)-pyrimidinetrione The acid chloride of step 3 (0.2 mole) in chloroform (75 mL) was added dropwise over 15 minutes to a mixture of benzyl 1-piperazinecarboxylate (6.0 g, 0.030 mole) and triethylamine (4.0 g, 0.04 mole) in chloroform (100 mL). This mixture was stirred at room temperature for 20 hrs, and dichloromethane was then added (300 mL). The mixture was washed with 10% hydrochloric acid solution (3×100 mL), washed with saturated sodium chloride solution (100 mL), dried over anhydrous magnesium sulfate, filtered, and the solvent removed. The residue was then chromatographed on SiO₂ to give a solid.

Step 5: Preparation of 5-Ethyl-5-phenyl-1-[4-(1-piperazinylcarbonyl)butyl]-2,4,6(1H,3H,5H)pyrimidinetrione Hydrobromide The protected amine from preparation 4 (6.5 g, 0.012 mole) and 30–35% hydrogen bromide-acetic acid solution (30 mL) was allowed to stir at room temperature for 1.5 hrs. The mixture was then poured into ethyl acetate (2 L), stirred for 1 hr, filtered, and the solid washed with 500 mL ethyl acetate.

Step 6: Preparation of 1-{4-[4-(3-Carboxypropionyl)-1-piperazinylcarbonyl]-butyl}-5-ethyl-5-phenyl-2,4,6(1H,3H,5H)-pyrimidinetrione The amine of step 5 (4.8 g, 0.01 mole), succinic anhydride (1.2 g, 0.012 mole), and triethylamine (2.2 g, 0.02 mole) in chloroform (150 mL) were heated for 30 min at 50°–60° C. (hot water) and allowed to stir at ambient temperature for 16 hrs. Dichloromethane (200 mL) was added, the mixture was washed with 10% hydrochloric acid solution (3×100 mL). saturated sodium chloride solution (100 mL), dried over anhydrous magnesium sulfate, filtered, and the solvent removed on a rotary evaporator in vacuo to give a white solid, 3.3 g (66%). This material was chromatographed using a SiO₂ column to give a white solid.

Step 7: Preparation of 5-Ethyl-5-phenyl-1-{4-[4-(3-Succinimidoxycarbonylpropionyl)-1-piperazinylcarbonyl]butyl}-2,4,6(1H,3H,5H)pyrimidinetrione

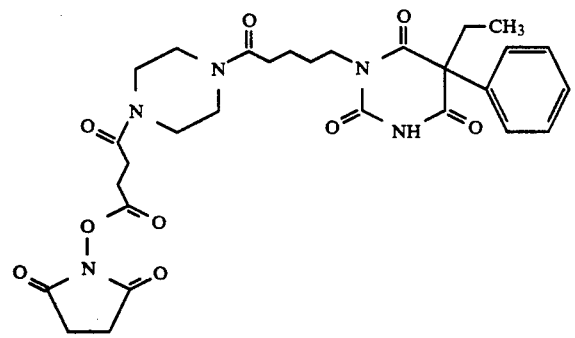

A mixture of the acid from step 6 (3.4 g, 0.007 mole), N,N'-dicyclohexylcarbodiimide (1.6 g, 0.008 mole), and N-hydroxysuccinimide (1.0 g, 0.008 mole) in chloroform (75 mL) was stirred at room temperature for 20 hrs. The mixture was filtered, and ethyl acetate (100 mL) was added. The organic solution was washed with water (2×100 mL), saturated sodium chloride solution (50 mL), dried over anhydrous magnesium sulfate, filtered, and the solvent removed on a rotary evaporator under vacuo. A portion of the solid was chromatographed to give a white solid.

Example 5 —Preparation of PB 2, 5-Ethyl-5-phenyl-2-(4-succinimidoxycarbonylbutyl)-2,4,6(1H,3H,5H)pyrimidinetrione

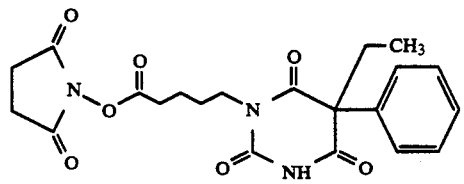

This material was prepared using the procedure of step 7, preparatory example 4 except starting with the acid of step 2. The material crystallizes from ethyl ether/ethyl acetate (1:1) to give a white solid.

Example 6 —Preparation of PB 3, 5-Ethyl-5-phenyl-1-{4-[2-(3-succinimidoxycarbonylpropionyloxy)ethylaminocarbonyl]butyl}-2,4,6(1H,3H,5H)pyrimidinetrione

Step 1: Preparation of 5-Ethyl-1-[4-(2-hydroxyethylaminocarbonyl)butyl]-5-phenyl-2,4,6(1H,3H,5H)pyrimidinetrione This material was prepared as outlined in step 4 of preparatory example 4 except using 2-hydroxyethylamine in place of the benzyl 1-piperazinecarboxylate.

Step 2: Preparation of 1-{4-[2-(3-Carboxypropionyloxy)ethylaminocarbonyl]-butyl}-5-ethyl-5-phenyl-2,4,6(1H,3H,5H)pyrimidinetrione A mixture of the product from step 1 (2.9 g, 0.007 mole), succinic anhydride (0.7 g, 0.007 mole), and dimethylaminopyridine (0.9 g, 0.007 mole) in chloroform (100 mL) was heated with hot water (50°–60° C.) for 30 min and then stirred at room temperature for 3 days. Dichloromethane (300 mL) was added, and the mixture was washed with 10% hydrochloric acid solution (2×100 mL), washed with saturated sodium chloride solution (100 mL), dried over anhydrous magnesium sulfate, filtered, and solvent removed to give an oil which was used directly in the next step.

Step 3: Preparation of PB 3, 5-Ethyl-5-phenyl-1-{4-[2-(3-succinimidoxycarbonylpropionyloxy)ethylaminocarbonyl]butyl}-2,4,6(1H,3H,5H)-pyrimidinetrion

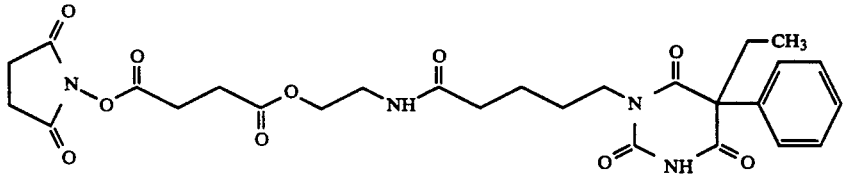

This material was prepared using the procedure outlined in step 7 of preparatory example 4 starting with the acid of step 2 of this example.

Example 7 —Preparation of PB 4, 5-Ethyl-5-phenyl-1-{4-[3-(3-succinimidoxycarbonyl-propionamido)propylaminocarbonyl]butyl}-2,4,6(1H,3H,5H)pyrimidinetrione

Step 1: Preparation of 1-[4-(3-Benzyloxycarbonylaminopropylaminocarbonyl)butyl]-5-ethyl-5-phenyl-2,4,6(1H,3H,5H)-pyrimidinetrione This material was prepared using the procedure outlined in step 4, preparatory example 4, except substituting N-benzyloxycarbonyl-1,3-propanediamine for the benzyl 1-piperazinecarboxylate, and the crude material was used in the next step.

Step 2: Preparation of 1-[4-(3-Aminopropylaminocarbonyl)butyl]-5-ethyl-5-phenyl-2,4,6(1H,3H,5H)-pyrimidinetrione Hydrobromide This material was prepared as in step 5, preparatory example 4 (except starting with the amide of step 1 of this example to give an oil when poured into ethyl ether.

Step 3: Preparation of 1-{4-[3-(3-Carboxypropionamido)propylaminocarbonyl]butyl}-5-ethyl-5-phenyl-2,4,6(1H,3H,5H)pyrimidinetrione This material was prepared by the procedure of step 6, preparatory example 4, except starting with the amine from step 2 of this example to give the acid.

Step 4: Preparation of PB 4, 5-ethyl-5-phenyl-1-{4-[3-(3-succinimidoxycarbonylpropionamido)propylaminocarbonyl]butyl}2,4,6,(1H,3H,5H)-pyrimidinetrione

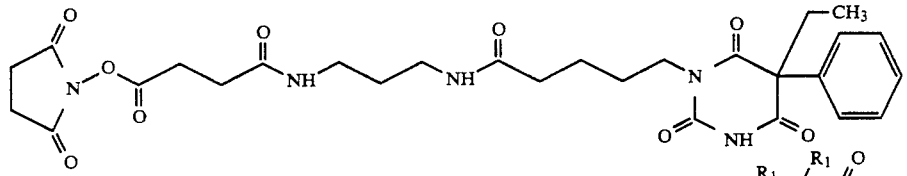

This material was prepared using the procedure of step 7, preparatory example 4 except starting with the acid of step 3 of this example.

Example 8 —Preparation of PB 5, 5-Ethyl-5-phenyl-1-{4-[6-(3-succinimidoxycarbonyl-propionamido)hexylaminocarbonyl]butyl}-2,4,6(1H,3H,5H)-pyrimidinetrione

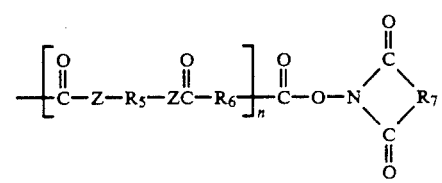

This compound was prepared by the sequence of reactions of preparation example 7 except substituting N-benzyloxycarbonyl-1,6-hexanediamine for the benzyloxycarbonyl-1,3-propanediamine in step 1, and the respective reaction products thereafter in steps 2, 3, and 4 of preparation example 7.

We have prepared new labeled drug hapten analogues from the drug hapten analogues of this invention that are useful in competitive immunoassays for drugs that possess the hydantoin or barbiturate nucleus, particularly phenytoin and phenobarbital. The labels are those commonly used in immunoassays with labels having an amine or sulfhydryl group such as enzymes.

The invention has been described in detail with particular reference to preferred embodiments thereof, but it will be understood that variations and modifications can be effected within the spirit and scope of the invention.

What is claimed is:

1. A drug hapten analogue conforming to structure I:

Structure I $$A-R_2 \left[ \begin{array}{c} O \\ \| \\ -C-N \end{array} \begin{array}{c} R_3 \\ \diagdown \\ \diagup \end{array} N-\begin{array}{c} O \\ \| \\ C-R_4 \end{array} \right]_m$$

$$\left[ \begin{array}{ccc} O & & O \\ \| & & \| \\ -C-Z-R_5-ZC-R_6 \end{array} \right]_n \begin{array}{c} O \\ \| \\ -C-O-N \end{array} \begin{array}{c} O \\ \| \\ C \\ \diagdown \\ \diagup \\ C \\ \| \\ O \end{array} R_7$$

wherein
A represents a hydration nucleus of the structure HN⟨ ⟩N—; or a barbituate nucleus of the structure HN⟨ ⟩N—; wherein $R^1$ each independently represents hydrogen, alkyl of 1 to 10 carbon atoms, or phenyl;

$R^2$ represents C1 to C10 alkylene or such alkylene groups interrupted with at least one or more ester groups, amide groups, —O—, —S—, or —NR—, wherein R represents hydrogen or $C_1$ to $C_6$ alkyl;

$R^4$, $R^5$, and $R^6$, each independently, represents phenylene, $C_1$ to $C_{10}$ alkylene or such alkylene groups interrupted with ester groups, amide groups, —O—, —S—, or —NR—, wherein R represents hydrogen or $C_1$ to $C_6$ alkyl;

$R^3$ represents $C_1$ to $C_3$ alkylene;

$R^7$ is an ethylene or o-phenylene;

Z represents —O—, —S—, or —NR—, wherein R represents hydrogen or $C_1$ to $C_6$ alkyl;

m is 0, 1, or 2;

n is 0, 1, or 2; and the total number of atoms comprised in m, n and $R^2$ is 5 to 40;

and further provided that (i) at least one of the $R^1$ groups is phenyl; (ii) the bracketed components of structure I can appear therein in any order and (iii) the linking group is other than a derivative of a saturated or unsaturated monocarboxylic acid having from to 2 to 12 carbon atoms.

2. The drug hapten analogue derivatives of claim 1 according to structure I wherein each $R^1$ independently represents phenyl or ethyl;

$R^2$ is butylene;

$R^3$, $R^4$, $R^5$ and $R^6$, each independently, represent ethylene or hexylene;

Z represents —O— or —NH; and $R^7$ represents ethylene.

3. The drug hapten analogue according to claim 1, selected from 5,5-Diphenyl-3-{4-[4-(3-succinimidoxycarbonylpropionyl)-1-piperazinylcarbonyl]butyl}-2,4-imidazolidinedione;

5,5-Diphenyl-3-{4-[2-(3-succinimidoxycarbonylpropionyloxy)ethylaminocarbonyl]butyl}-2,4-imidazolidinedione 5,5-Diphenyl-3-{4-[6-(3-succinimidoxycarbonylpropionamido)hexylaminocarbonyl]butyl}-2,4-imidazolidinedione.

5-Ethyl-5-phenyl-1-{4-[6-(3-succinimidoxycarbonylpropionamido)hexylaminocarbonyl]butyl}-2,4,6(1H,3H,5H)-pyrimidinetrione 5-Ethyl-5-phenyl-1-{4-[3-(3-succinimidoxycarbonylpropionamido)propylaminocarbonyl]butyl}-2,4,6(1H,3H,5H)-pyrimidinetrione 5-Ethyl-5-phenyl-1-{4-[2-(3-succinimidoxycarbonylpropionyloxy)ethylaminocarbonyl]butyl}-2,4,6(1H,3H,5H)-pyrimidinetrione 5-Ethyl-5-phenyl-2-(4-succinimidoxycarbonylbutyl)-2,4,6(1H,3H,5H)pyrimidinetrione and 5-Ethyl-5-phenyl-1-(4-[4-(3-Succinimidoxycarbonylpropionyl)-1-piperazinylcarbonyl]butyl}-2,4,6(IH,3H,5H)pyrimidinetrione.

* * * * *